United States Patent
Bouali et al.

(10) Patent No.: US 6,482,813 B1
(45) Date of Patent: Nov. 19, 2002

(54) STEROIDS SUBSTITUTED AT THE 11-POSITION, PROCESS FOR THEIR PREPARATION, THEIR USE AS MEDICAMENT AND THE PHARMACEUTICAL COMPOSITIONS CONTAINING THEM

(75) Inventors: Yamina Bouali, Villejuif (FR); Francois Nique, Le Perreux sur Marne (FR); Jean-Georges Teutsch, Pantin (FR); Patrick Van De Velde, Paris (FR)

(73) Assignee: Aventis Pharma S.A. (FR)

( * ) Notice: Subject to any disclaimer, the term of this patent is extended or adjusted under 35 U.S.C. 154(b) by 0 days.

(21) Appl. No.: 09/592,710

(22) Filed: Jun. 13, 2000

Related U.S. Application Data

(62) Division of application No. 09/331,823, filed as application No. PCT/FR97/02379 on Oct. 4, 1999, now Pat. No. 6,207,657.

(30) Foreign Application Priority Data

Dec. 23, 1996 (FR) .............................. 96 15829

(51) Int. Cl.$^7$ ..................... A61K 31/585; A61K 31/58; A61K 31/56; C07J 7/00; C07J 9/00
(52) U.S. Cl. ..................... 514/182; 514/176; 514/178; 514/182; 514/175; 552/558; 552/540; 552/569; 552/586
(58) Field of Search ................. 514/178, 175, 514/176, 182; 552/558, 540, 569, 586

(56) References Cited

U.S. PATENT DOCUMENTS 4,859,585 A * 8/1989 Somenschein et al. ........ 435/29
5,981,516 A * 11/1999 Bounali et al. ............. 514/175

FOREIGN PATENT DOCUMENTS

EP 0384842 * 8/1990
EP 0642071 * 3/1995
FR 02640977 * 6/1990

OTHER PUBLICATIONS

Rousel–UCLAF (CA 114:102554, abstract of FR 2640977, (1990).*

Lu Jin et al. (Steroids, vol. 60, No. 8, (Aug. 1995), pp. 512–518).*

* cited by examiner

*Primary Examiner*—Sabiha Qazi
(74) *Attorney, Agent, or Firm*—Bierman, Muserlian and Lucas

(57) ABSTRACT

Compounds of formula

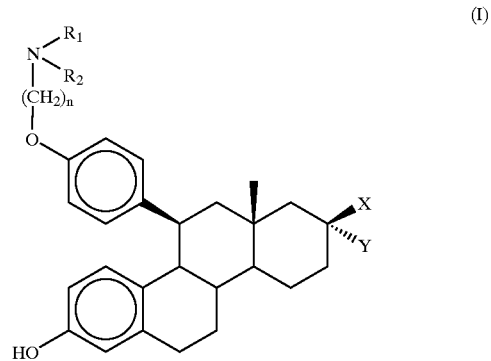

(I)

for treating osteoporosis with minimal estrogenic activity are disclosed.

9 Claims, No Drawings

STEROIDS SUBSTITUTED AT THE 11-POSITION, PROCESS FOR THEIR PREPARATION, THEIR USE AS MEDICAMENT AND THE PHARMACEUTICAL COMPOSITIONS CONTAINING THEM

PRIOR APPLICATION

This application is a division of U.S. patent application Ser. No. 331,823 filed Oct. 4, 1999 now U.S. Pat. No. 6,207,657 which is a 371 of PCT/FR97/02379 filed Dec. 22, 1997.

The present invention relates to steroid compounds substituted in position 11, the method of preparation, their application as medicine and pharmaceutical compositions containing them.

Osteoporosis is a pathology that is characterized by a quantitative and qualitative reduction of bone tissue, sufficient to lead to vertebral or peripheral fractures, occurring spontaneously or as a result of minimal trauma. Although this disorder is of multifactorial origin, in women the menopause is the predominant factor in bone loss or osteopenia.

This osteopenia is manifested by rarefaction and alteration of the architecture of the spongy bone which leads to increased fragility of the skeleton and increase in the risk of fractures. Bone loss increases considerably after the menopause owing to the decline in ovarian function and reaches 3 to 5% per year, but then slows down after the age of 65 years.

With a view to therapy, the hormone deficiency after the menopause can be compensated by hormone replacement therapy, in which oestrogen plays a major role by preserving bone mass. In the long term, however, oestrogen therapy is sometimes accompanied by undesirable effects on the genital system (endometrial hyperplasia, mammary tumours etc.), which constitutes a major drawback and limits its application.

It is therefore necessary to find compounds other than oestradiol that possess dissociated oestrogen activity, i.e. oestrogen activity in the bone tissue, yet with little or no activity of endometrial hyperplasia, nor activity of proliferation of mammary tumours.

The invention therefore relates to compounds of general formula (I):

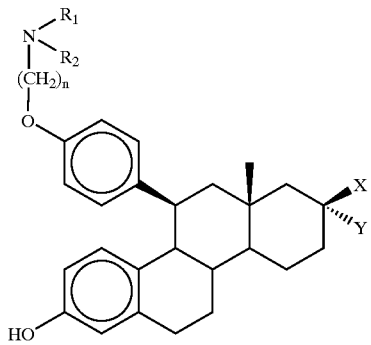

(I)

in which:
n is an integer equal to 2 or 3,
either $R_1$ and $R_2$, which may be identical or different, represent a hydrogen atom or an alkyl radical containing from 1 to 4 carbon atoms,
or $R_1$ and $R_2$ form, together with the nitrogen atom to which they are bound, a heterocycle., mono or polycyclic, saturated or unsaturated, of 5 to 15 units, aromatic or non-aromatic, optionally containing from 1 to 3 additional heteroatoms selected from oxygen, sulphur and nitrogen, substituted or unsubstituted,
X represents a hydroxyl radical, optionally esterified, and
Y represents an alkyl radical containing from 1 to 4 carbon atoms, as well as their pharmaceutically acceptable salts of addition with acids.

Alkyl radical containing from 1 to 4 carbon atoms unsubstituted or substituted is taken to mean methyl, ethyl, propyl, isopropyl, n-butyl, isobutyl and tert-butyl radicals.

when Y is substituted alkyl, it is preferably alkyl substituted with at least one halogen and preferably Y is trifluoro methyl.

When $R_1$ and $R_2$ form, together with the nitrogen atom to which they are bound, a heterocycle, this means in particular saturated mono or bicyclic heterocycles optionally containing:
another heteroatom selected from oxygen and nitrogen, such as heterocycles selected from: pyrrolyl, imidazolyl, indolyl, pyridyl, pyrazinyl, pyrimidinyl, pyridazinyl, thiazolyl, oxazolyl, furazonyl, pyrazolinyl, thiazolinyl, and quite particularly the following saturated heterocycles:

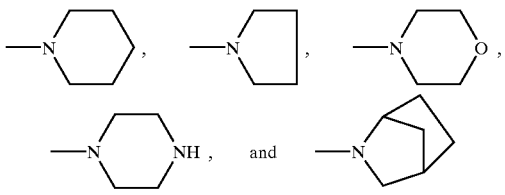

When this heterocycle is substituted, it is substituted in particular by an alkyl group containing from 1 to 4 carbon atoms on the nitrogen atom.

When X is a hydroxyl radical, optionally esterified, we mean the OCO—alc1 groups in which alc1 is an alkyl radical containing from 1 to 8 carbon atoms and preferably the groups —OCOMe and OCOEt.

By pharmaceutically acceptable salts of addition with acids, we mean salts of addition formed with inorganic or organic acids on the amine. Possible acids are hydrochloric, hydrobromic, nitric, sulphuric, phosphoric, acetic, formic, propionic, benzoic, maleic, fumaric, succinic, tartaric, citric, oxalic, glyoxylic, aspartic, alkanesulphonic such as methane- or ethane-sulphonic acids, arylsulphonic acids, such as benzene- or paratoluene-sulphonic acids and arylcarboxylic acids.

The invention relates more particularly to the compounds of formula (I) as defined above in which n is equal to 2, as well as their pharmaceutically acceptable salts of addition with acids.

The invention relates more particularly to the compounds of formula (I) as defined above in which:
n is equal to 2,
either $R_1$ and $R_2$, which may be identical or different, represent an alkyl radical containing from 1 to 4 carbon atoms,
or $R_1$ and $R_2$ form, together with the nitrogen atom to which they are bound, a piperidino, pyrrolidino or 2-azabicyclo(2.2.1)hept-2-yl group,
X represents a hydroxyl radical and Y represents a methyl or ethyl radical.

The invention relates quite particularly to compounds of formula (I) as well as their pharmaceutically acceptable salts of addition with acids, with the following names:

11β-[4-[2-(1-piperidinyl)ethoxy]phenyl]-19-nor-17α-pregna-1,3,5(10)-triene-3,17β-diol, 17α-methyl-11β-[4-[2-(1-piperidinyl)ethoxy]phenyl]-oestra-1,3,5(10)-triene-3,17β-diol, 17α-methyl-11-[4-[2-(diethylamino)ethoxy]phenyl]-oestra-1,3,5(10)-3,17β-diol, 17α-methyl-11β-[4-[2-(1-pyrrolidinyl)ethoxy]phenyl]-oestra-1,3,5(10)-triene-3,17β-diol, 17α-methyl-11β-[4-[2-(2-aza-bicyclo(2.2.1)hept-2-yl)ethoxy]phenyl]-oestra -1,3,5(10)-triene-3,17β-diol, 11β-[4-[2-(2-aza-bicyclo(2.2.1)hept-2-yl)ethoxy] phenyl]-19-nor-17α-pregna-1,3,5(10)-triene-3,17β-diol, 17α-(trifluoromethyl)11β-[4-[2-(1-piperidinyl)ethoxy] phenyl]oestra-1,3,5(10)-triene-3,17β-diol.

The invention also relates to a method of preparation of the compounds of general formula (I) as defined previously, characterized in that a compound of general formula (II):

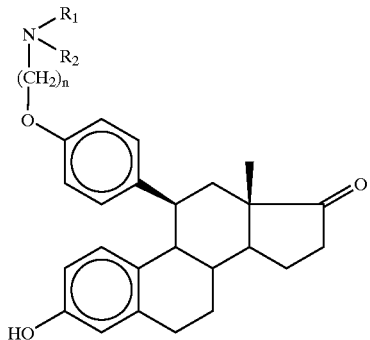

(II)

in which n, $R_1$ and $R_2$ are as defined previously, is submitted to the action of an organometallic compound containing from 1 to 4 carbon atoms so as to form the compounds of formula (I) in which X is a hydroxyl group and Y is an alkyl group containing from 1 to 4 carbon atoms, and this compound of formula (I) is submitted if necessary to a reaction of esterification of the 17-OH and/or to a reaction of salification.

The action of an organometallic on the 17-keto group provides access to products of formula (I) in which X is a hydroxyl group and Y is an alkyl group containing from 1 to 4 carbon atoms.

The organometallic compound derived from an alkyl radical containing from 1 to 4 carbon atoms is selected from among the magnesium compounds of formula Y—MgHal and the lithium compounds of formula Y—Li in which Y is as defined previously and Hal represents a halogen atom. Preferably the reaction takes place in the presence of cerium chloride. In a preferred manner of carrying out the method, Hal represents an atom of chlorine, bromine or iodine, preferably bromine.

To obtain compounds of formula (I) in which X is an hydroxyl radical and Ya $CF_3$ group, the reaction is effected by the action of $CF_3SiMe_3$ on the 17-keto followed by the action of a deprotection agent such as tetrabutylammonium flouride.

The invention also relates to a method of preparation of compounds of general formula (I) as defined previously, with Y representing an alkyl radical containing from 2 to 4 carbon atoms, characterized in that a compound of general formula (III):

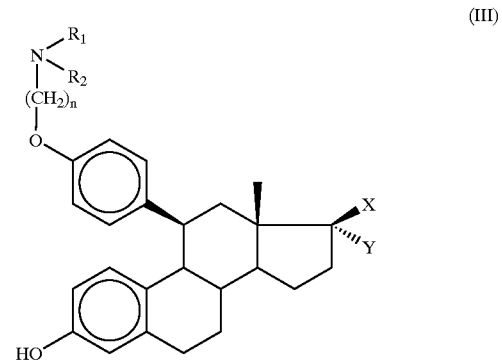

(III)

in which n, $R_1$ and $R_2$ are as defined previously and in which Y' represents an alkenyl or alkynyl group containing from 2 to 4 carbon atoms, is submitted to the action of a reducing agent of the double bond or of the triple bond, so as to obtain compounds of formula (I) in which X is a hydroxyl group And Y is an alkyl group containing from 1 to 4 carbon atoms, this compound of formula (I) being submitted if necessary to a reaction of esterification of the 17-OH, and/or to a reaction of salification.

The reaction of complete reduction can be carried out by the action of hydrogen in the presence of a catalyst such as palladium on carbon or a rhodium catalyst such as Wilkinson's reagent.

The reactions of esterification and salification are carried out by the usual methods known by a person skilled in the art The compounds of general formula (I) as well as their pharmaceutically acceptable salts of addition with acids possess oestrogen activity, anti-oestrogen activity and anti-proliferative activity.

On this basis, the compounds of formula (I) can be used, in the treatment of disorders connected with hypofolliculinism, for example amenorrhoea, dysmenorrhoea, repeated miscarriages, premenstrual disorders, in the treatment of certain oestrogen-dependent pathologies such as adenomas or carcinomas of the prostate, carcinomas of the breast and their metastases or in the treatment of benign breast tumours, as anti-uterotrophic as well as in replacement therapy of the menopause or perimenopause.

The symptoms and consequences connected with the menopause are, more precisely: hot flushes, sweating, atrophy and dryness of the vagina, urinary symptoms and in the long term decrease in bone mass and increased risk of fracture, as well as the loss of cardiovascular protection afforded by the oestrogens.

In particular, the compounds of formula (I) as well as their pharmaceutically acceptable salts of addition with acids, can thus be used in the prevention or treatment of osteoporosis.

The compounds of formula (I) as well as their pharmaceutically acceptable salts of addition with acids can also be used in the prevention or treatment of osteoporosis in humans.

They can also be used in the prevention or treatment of secondary osteoporosis (for example cortisone-related osteoporosis, associated with immobilization).

The compounds of formula (I) as well as their pharmaceutically acceptable salts of addition with acids possess, in particular, a dissociated oestrogen activity.

Dissociated oestrogen activity means oestrogen activity in the bone which only exhibits minimal activity in the uterus, and so does not lead to enddmetrial proliferation (activity well below that of oestradiol).

Furthermore, the compounds according to the invention offer the following advantages:

They exhibit anti-oestrogen activity in the breast. In contrast to oestradiol, they do not stimulate the growth of human mammary tumour cells and can even inhibit their growth. The compounds according to the invention are therefore particularly advantageous for the treatment of the menopause in women at risk from breast cancer (family history) who are therefore excluded from replacement therapy with oestradiol. They can also be used in the treatment of breast cancers.

They lead to a lowering o the serum cholesterol level to a level equivalent to that induced by oestradiol. They thus reinforce cardiovascular protection.

Finally, the compounds according to the invention do not exhibit oestrogen activity in the uterus and so do not require to be administered in conjunction with a progestomimetic compound.

The invention therefore relates to compounds of general formula (I), as well as their pharmaceutically acceptable salts of addition with acids, as medicines.

The invention relates more particularly to the compounds of formula (I) as well as their pharmaceutically acceptable salts of addition with acids, as medicines for the prevention or treatment of osteoporosis.

The invention relates quite particularly to the compounds or general formula (I), as well as their pharmaceutically acceptable salts of addition with acids, as medicine intended for the prevention or treatment of osteoporosis, which exhibit little or no oestrogen activity on the uterus.

Finally the invention relates quite particularly to the compounds of general formula (I), as well as their pharmaceutically acceptable salts of addition with acids, as medicine intended for the prevention or treatment of osteoporosis in women at risk from mammary tumours.

The invention covers pharmaceutical compositions containing as active principle at least one of the medicines as defined above.

The compounds of formula (I) as well as their pharmaceutically acceptable salts of addition with acids, are administered via the alimentary canal, or parenterally or locally, for example percutaneously. They can be prescribed in the form of plain or coated tablets, capsules, granules, suppositories, pessaries, injectable preparations, ointments, creams) gels, microspheres, implants, intravaginal rings, patches, sprays, which are prepared by the usual methods.

The active principle or principles can be incorporated in them with the excipients usually employed in these pharmaceutical compositions, such as talc, gum arabic, lactose, starch, magnesium stearate, cocoa butter, aqueous or non-aqueous vehicles, fatty substances of animal or vegetable origin, paraffinic derivatives, glycols, the various wetting, dispersing or emulsifying agents, and preservatives.

The posology required varies according to the disorder to be treated and the route of administration; for example it can vary from 0.5 to 100 mg per day for an adult when taken orally.

The compounds of general formula (II) and (III) are known compounds that are described in the following patents: EP-B-0097572, FR-B-2640977, EP-B-305942.

The examples given below illustrate the invention though without limiting it.

EXAMPLE 1

17α-Methyl-11β-[4-[2-(1-piperidinyl)ethoxy] phenyl]-oestra-1,3,5(10)-triene-3,17β-diol Dehydrate 1.056 g of $CeCl_3$ (III), $7H_2O$ under reduced pressure at 140° C. then add, under an inert atmosphere and at room temperature, 10.6 ml of tetrahydrofuran (THF) then, after stirring for 2 hours, add at −70° C., 89 ml of ether solution of methyllithium 1.6M and stir for 30 minutes at −75° C. Next, add to this suspension 268 mg of 3-hydroxy-11β-[4-[2(1-piperidinyl)ethoxy]phenyl]-oestra-1,3,5(10)-trien-17-one in solution in 3-ml of THF/siliorite and stir at this temperature for 1 hour.

After adding 15 ml of a saturated solution of ammonium chloride and 20 ml of ethyl acetate, filter, wash, dry and evaporate under reduced pressure to obtain 277 mg of the expected raw product. Purify this product by chromatography on a column of silica, eluting with mixture of methylene chloride 90/methanol 10/ammonium hydroxide 0.5. We obtain 232 mg of product, which is recrystallized in dichloromethane/isopropyl ether mixture, obtaining 180 mg of the expected pure product.

| | |
|---|---|
| F = 155° C. | |
| IR ($CHCl_3$) | |
| —OH | 3602 $cm^{-1}$ + general absorption |
| aromatic | 1610 $cm^{-1}$, 1580 $cm^{-1}$, 1512 $cm^{-1}$ |
| NMR ($CDCl_3$) | |
| 0.51 (s) | Me 18 |
| 1.29 (s) | Me at 17 |
| 3.98 (m) | $O-CH_2-CH_2-N$, CH—Ph ($H_{11}$) |
| 6.41 | $H_2$, $H_4$ ring A, $H'_3$, $H'_5$ of the phenyl at 11 |
| 6.78 (d) | $H_1$ of ring A |
| 6.94 | $H'_2$, $H'_6$ of the phenyl at 11 |

EXAMPLE 2

11β-[4-[2-(1-Piperidinyl)ethoxy]phenyl]-19-nor-17α-pregna-1,3,5(10)-triene-3,17β-diol Under an inert atmosphere, to a solution of 192 mg of 11β-[4-[2-(1-piperidinyl)ethoxy]phenyl]-19-nor-17α-pregna-1,3,5(10)-trien-20-yne-3,17β-diol in 6 ml of ethanol, add 20 mg of palladium on activated carbon (9.5%) and stir under pressure of 1660 mbar of hydrogen for 1 hour 45 minutes. Filter the suspension and evaporate under reduced pressure. 193 mg of raw product is obtained, which is purified by chromatography on an attached-silica column (Lichrosorb RP18), eluting with mixture of methanol 90/water 10.137 mg of product is obtained, which is recrystallized in dichloromethane/isopropyl ether mixture, obtaining 114 mg of the pure product expected. F=231° C.

| | |
|---|---|
| IR ($CHCl_3$) | |
| —OH | 3600 $cm^{-1}$ + general absorption |
| aromatic | 1610 $cm^{-1}$, 1581 $cm^{-1}$, 1512 $cm^{-1}$ |
| NMR ($CDCl_3$ + 2 drops of $C_5D_5N$) | |
| 0.47 (s) | Me 18 |
| 1.01 (t) | $CH_2-CH_3$ |
| 2.47 | $-CH_2-N-CH_2-$ (piperidine) |
| 2.71 | $O-CH_2-CH_2-N$ |
| 3.99 (m) | $O-CH_2-CH_2-N$, CH—Ph ($H_{11}$) |
| 6.48 (dd) | $H_2$ |
| 6.59 | $H'_3$, $H'_5$ (phenyl at 11) |
| 6.63 (d) | $H_4$ (ring A), |
| 6.80 (d) | $H_1$ (ring A) |
| 6.96 | $H'_2$, $H'_6$ of the phenyl at 11 |
| 9.94 | 3-OH |

EXAMPLE 3

11β-[4-[2-[2-Azabicyclo(2,2,1)hept -2-yl]ethoxy] phenyl]17α-methyL-oestra-1,3,5(10)-triene-3-17β-diol One operates as in EXAMPLE 1 using at the start 3.70 g. of $CeCl_3$. $7H_2O$ and 37 ml of tetrahydrofuran at 6.7 ml of ethereal solution of methyllithium (1.6M). To the suspension obtained cooled to −78° C., one slowly adds 966 mg 11β-[4,[2-[2,azabicyclo(2,2,1)hept-2-yl]ethoxyl]phenyl]3-hydroxyoestra 1,3,5(10)triene-17-one in solution of 8 ml of tetrahydrofuran, agitates for 45 minutes and continues the synthesis as is Example 1. One obtains 874 mg of crude product. After chromatography over silica (eluant: $CH_2Cl_2$—$NH_4OH$ 90-10-0.7 AcOEt–TEA 88-12) one obtains 442 mg of the expected product. M.pt.=163–164° C.

| IR ($CHCl_3$) | |
|---|---|
| —OH | 3602 cm$^{-1}$ + general absorption |
| aromatic | 1610 cm$^{-1}$, 1581 cm$^{-1}$ 1512 cm$^{-1}$ |
| NMR ($CDCl_3$) | |
| 0.51 (s) | Me at 18 |
| 1.29 (s) | Me at 17 |
| 3.85 to 4.05 | O—$CH_2$—N, CH—Ph ($H_{11}$) |
| 6.41 | $H_2$, $H_4$ ring A |
| 6.77 | $H_1$ of ring A |
| 6.46–6.95 | H of phenyl at 11 |

Preparation of the 11β-(4-[2-[2 azabicyclo(2,2,1)hept-2-yl]ethoxy]phenyl]3-hydroxyoestra-1,3,5(10)-triene-17-one used at the start of the Example 3.

One mixes 1.1 g of 3-hydroxy 11β-[4-(iodoethoxy) phenyl]oestra-1,3,5(10)-triene-17-one in solution in 20 ml of tetrahydrofuran and 1.03 g of 2-azabicyclo[2,2,1,]heptane and agitates for 1 hour and a half at reflux temperature under a nitrogen atmosphere. One evaporates off the tetrahydrofuran, takes up the residue in ethyl acetate, adds water, extracts with ethyl acetate, dries, evaporate off the solvent and after chromatography over silica (eluant $CH_2Cl_2$—$CH_3OH$—$NH_4OH$ 90-10-0.5) obtains 0.97 g of the expected product.
Rf=0.27.

EXAMPLE 4

17α-Methyl 11β-[4-[2-(1-pyrrolidinyl)ethoxy]phenyl]oestra-1,3,5(10)-triene-3,17β-diol One operates as in Example 1 using at the start 3.24 g of CeCl3. $7H_2O$, 30 ml of tetrahydrofuran 5.85 ml of methyllithium then 850 mg of 3-hydroxy 11β-[4-[2-(1-pyrrolidinyl)ethoxy]phenyl]oestra-1,3,5(10)-triene-17 one in solution 8.5 ml of tetrahydrofuran. After chromatography over silica (eluant: CH2CL2—CH3OH—NH4OH 92-8-0.5) one obtains 615 mg of the expected product. M.pt. 155–157° C.

| IR (CHCl3) | |
|---|---|
| —OH | 3603 cm$^{-1}$ + general absorption |
| aromatic | 1610 cm$^{-1}$, 1581 cm$^{-1}$, 1512 cm$^{-1}$ |
| NMR ($CDCL_3$) | |
| 0.51 (s) | Me at 18 |
| 1.29 (s) | Me at 17 |
| 3.99 | O—$CH_2$—$CH_2$—N, CH—Ph ($H_{11}$) |
| 6.38 (dd) | $H_2$ ring A |
| 6.40 (d) | $H_4$ ring A, |
| 6.77 (d) | $H_1$ ring A |
| 6.49–6.95 | H of the phenyl at 11 |

Preparation of 3-hydroxy 11β-[4-[2(1-pyrrolidinyl)ethoxy]phenyl]oestra-1,3,5(10)-triene 17-one used at the beginning Example 4.

One operates as in the preparation of the starting product of Example 3 employing 1.1 g of the iodo steroid derivative in 20 ml tetrahydrofuran and 1 ml of pyrrolidine. One obtains 864 mg of the expected product after chromatography over silica (eluant CH2CHl2—CH3OH—NH4OH 92-8-0.2). Rf=0.29.

EXAMPLE 5

11β-[4-[2-(Diethylamino)ethoxy]phenyl]17α-methyloestra-1,3,5(10)triene-3,17β-diol One operates as in Example 1 using at the start 3.62 g of the chloride of $CeCl_3$. $7H_2O$, 36 ml of tetrahydrofuran and 6.5 ml methyllithium in ether (1.6 m) then 898 mg of 3-hydroxy 11β-[4-[2-(diethylamino) ethoxy]phenyl]oestra 1,3,5(10)-triene-17 one in solution in 9 ml tetrahydrofuran. After chromatography over silica (eluant: $CH_2CL_2$—$CH_3OH$—$NH_4OH$ 92-8-0.5) one obtains 686 mg of the expected product. M.pt.=159–160° C.

| IR ($CHCl_3$) | |
|---|---|
| —OH | 3602 cm$^{-1}$ + general absorption |
| aromatic | 1610 cm$^{-1}$, 1581 cm$^{-1}$, 1512 cm$^{-1}$ (F) , 1500 cm$^{-1}$ (ep) |
| NMR ($CDCl_3$) | |
| 0.47 (s) | Me 18 |
| 1.05 (t) | —N—($CH_2$—$CH_3$)$_2$ |
| 1.28 (s) | Me at 18 |
| 2.65 (m) | —N—($CH_2$—$CH_3$)$_2$ |
| 3.95 (t) | O—$CH_2$—$CH_2$—N, |
| 6.31 (d) | $H_4$ (ring A) |
| 6.38 (dd) | $H_2$ (ring A) |
| 6.80 (d) | $H_1$ (ring A) |
| 6.56 and 6.93 | H of the phenyl at 11 |

Preparation of the 3-Hydroxy 11β-[4-[2-(diethylamino)ethoxy]phenyl]oestra-1,3,5(10)-triene-17-one.

One operates as in the preparation of the starting product for Example 3 using 1.1 g of the iodo steroid derivative in 20 ml tetrahydrofuran and 2 ml diethylamine. One obtains 898 mg of the expected product after chromatography over silica (eluant: $CH_2Cl_2$—$CH_3OH$—$NH_4OH$ 92-8-0.2). Rf-0.24.

EXAMPLE 6

17α-(Trifluoromethyl)11β-[4-[2-(1-Piperidinyl)ethoxy]phenyl]oestra-1,3,5(10)-triene-3,17β-diol One heats for 2 hours at 120° C. under 10-2 mbar 83 mg of tetrabutylammonium fluoride (Me4NH. 4H2O) then allows it to come back to ambient temperature under an inert atmosphere. One adds to 237 mg of 3 hydroxy 11β-[4-[2-(1-piperidinyl)ethoxy]phenyl]oestra-1,3,5(10)-triene-17 one in solution in 3 ml of tetrahydrofuran, cools to +4° C. and adds 0.3 ml of trimethyl (trifluromethyl)-silane then agitates for 2 hours at this temperature. One adds 4 ml of tetrahydrofuran, agitates for 3 hours and a half at ambient temperature, adds water, extracts with methylene chloride, washes with water, dries and evaporates off the solvents under reduced pressure. One chromatographs the residue over silica (eluant: $CH_2Cl_2$—MeOH—$NH_4OH$ 9-10-0.1) and obtains 127 mg o the expected product.

| IR ($CHCl_3$) | |
|---|---|
| —OH | 3598 cm$^{-1}$ + general absorption |
| aromatic | 1610 cm$^{-1}$, 1580 cm$^{-1}$, 1512 cm$^{-1}$ |
| NMR ($CDCl_3$) | |
| 0.56 (s) | Me 18 |

-continued

| | |
|---|---|
| 4.00 (m) | O—CH$_2$—CH$_2$—N, CH—Ph (H$_{11}$) |
| 6.37 (dd) | H$_2$ (ring A) |
| 6.41–6.93 | H'$_2$, H'$_3$ (phenyl at $_{11}$) |
| 6.41 (d) | H$_4$ (ring A) |
| 6.77 (d) | H$_1$ (ring A) |

Pharmacological Tests

1) Effect on proliferation of mammary cells

The proliferative activity of the molecules is investigated in comparison with that of oestradiol on human mammary cells MCF-7 in culture.

To demonstrate an agonistic effect of oestradiol and/or of the molecules tested, the culture medium for maintenance of the cells (rich in growth factors and in steroids) is replaced by an impoverished medium, devoid of steroids among others (DMEM supplemented with 5% of desteroidized serum and without phenol red). The cells undergo this deprivation two days before commencement of the test.

After 7 days of culture in the presence of the products under investigation, cell proliferation is evaluated by assay of the DNA. In each test, the effect of oestradiol at $10^{-10}$M (cell growth in the presence of oestradiol less cell growth in the presence of the solvent) determines 100% agonistic activity. The activity of the molecules is evaluated in comparison with this internal standard. Molecules providing call growth identical to that observed with the solvent alone are graded as "inactive", those giving cell growth less than that observed with the solvent are graded as "inhibitory".

| | E2 | Ex. 2 | Ex. 3 |
|---|---|---|---|
| Activity | Agonistic | Inactive | inhibitory |

2) The compounds according to the invention are tested to determine their effect on bone mass and on activity of formation an resorption in the model of the female rat ovariectomized at the age of three months. The animals receive preventive treatment.

| Animals: | |
|---|---|
| Species | rat |
| Strain | Sprague-Dawley |
| Sex | Female |
| Weight | 250 g to 280 g |
| Number of animals/group | 8 |

Products:
Test product: Product from Example 1.
   vehicle(s): corn oil. methylcellulose 0.5%
   dose(s): one dose per test product [0.3 mg/kg/day]
   number of administrations: once/day; 5 days/week for 4 weeks
   route of administration: orally for the products
   volumes: 5 ml/kg (p.o.)
   time between last injection and sacrifice: 24 hours
   number of administrations: 20.
2—Reference product: 17β oestradiol is administered subcutaneously at a dose of 0.1 mg/kg/day in solution in a mixture of naize-germ oil-benzyl alcohol (99:1, v/v) under a volume of 0.2 ml/kg.

Experimental procedure

Animals

The study is conducted on female rats ovariectomized at the age of 3 months. The animals are kept in an air-conditioned room (temperature 20° C.±2° C.) with groups of 4 in the boxes. The animals receive, ad libitum, demineralized water and compressed foods (pellets: A04CR-10 UAR).

Surgery

Female rats aged 3 months, weighing about 250 g, are ovariectomized under anaesthesia with Imalgene 1000, at a dose of 100 mg/kg intraperitoneally (i.p.) and under a volume of 1 ml/kg. They also receive Nembutal (3 mg/kg i.p. under a volume of 0.3 ml/kg).

After lateral incision, the layers of skin and muscle are sectioned. Excision of each ovary is performed after ligature of the oviduct.

The "SHAM" control rats are anaesthetized in the same conditions. After incision of the layers of skin and muscle, each ovary is exposed and then replaced in situ.

Treatment

The effects of the products are determined in preventive treatment. They are administered immediately after ovariectomy. The animals are divided into groups of 8.

Group 1: "SHAM" control rats receiving the vehicle or vehicles

Group 2: "OVX" control rats receiving the vehicle or vehicles

Groups X: "OVX" rats receiving respectively the stated doses of the product or products to be tested.

Blood Samples

At the end of the 4 weeks (duration of the study) the animals are decapitated by guillotine. The sera collected after centrifugation are stored at −20° C.

A lipid balance is to drawn up from serum assays of total cholesterol, triglycerides and phospholipids on a 500 βl aliquot of serum. The drop in serum cholesterol level is expressed as a percentage in relation to the level found for the ovariectomized animals receiving the solvent alone.

Organ Samples

After sacrifice of the animals, the following organs are removed:

genital tract

The uteri are removed. They are weighed. The increase in weight is expressed as a percentage of the weight of the uterus of the ovariectomized animals that only received the solvent.

bone:

The bone mass (BMD or Bone Mineral Density) is measured by double-energy X-ray two-photon absorptiometry (DEXA). The measurements are performed on the bones after excision and after all soft tissues have been removed. The BMD is measured on the whole bone and on the metaphysis region at the proximal end for the left tibia. This zone is defined as being the region that is richest in trabecular bone; and consequently, it is the most sensitive to changes in bone volume and bone mineral density.

The results are expressed as a percentage according to the formula:

| | Dose mg/kg | OS TIBIA Density % | UTERUS weight % | Cholest. % |
|---|---|---|---|---|
| E2 | 0.1 sc | 105 | 359 | 35 |
| Ex. 1 | 0.3 po | 75 | 76 | −43 |
| Ex. 3 | 0.3 po | 46 | 37 | −48 |
| OVX | | 0 | | |
| SHAM | | 100 | | |

$$\frac{\text{BMD test product} - \text{BMD OVX}}{\text{BMD SHAM} - \text{BMD OVX}} \times 100$$

Conclusions

The compound according to the invention offer effective bone protection (−75%) while exhibiting minimum uterotrophic activity in comparison with that caused by oestradiol. Moreover, a significant drop in total cholesterol level is observed.

What is claimed is:

1. A compound selected from the group consisting of a compound of the formula

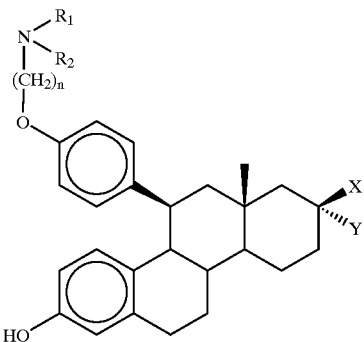

(I)

2. A compound of claim 1 wherein n is 2.
3. A compound of claim 1 wherein n is 2 and $R_1$ and $R_2$ are individually alkyl of 1 to 4 carbon atoms, X is —OH and Y is methyl or ethyl.
4. A compound of claim 1 which is 17α-methyl-11β-[4-(2-diethylaminoethoxy)-phenyl]-$\Delta^{1,3,5,(10)}$-estratriene-3,17β-diol and its acid addition salts.
5. A process for preparing a compound of claim 1 comprising reacting a compound of the formula

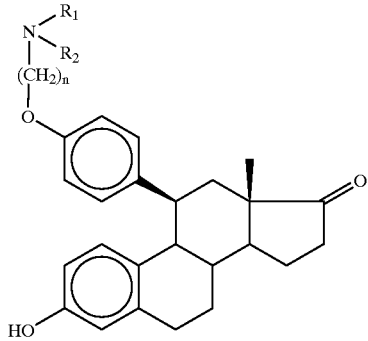

(II)

wherein n, $R_1$ and $R_2$ are defined as in claim 1 with an organometallic compound with alkyl of 1 to 4 carbon atoms to form a compound of claim 1 wherein X is —OH and Y is alkyl of 1 to 4 carbon atoms and optionally esterifying the 17β-ol with an organic carboxylic acid of 1 to 7 carbon atoms.

6. A composition for treating osteoporosis without estrogenic activity on the uterus comprising an anti-osteoporosis effective amount of a compound of claim 1 and an inert pharmaceutical carrier.

7. A method of treating osteoporosis with minimal estrogenic activity on the uterus in women comprising administering to women an amount of a compound of claim 1 sufficient to treat osteoporosis without estrogenic activity on the uterus.

8. A compound of claim 1 wherein Y is trifluoromethyl.
9. The method of claim 7 wherein Y is —$CF_3$.

* * * * *